(12) United States Patent
Freilich et al.

(10) Patent No.: US 6,599,125 B1
(45) Date of Patent: Jul. 29, 2003

(54) PREFABRICATED COMPONENTS FOR DENTAL APPLIANCES

(75) Inventors: Martin A. Freilich, West Hartford, CT (US); Jonathan C. Meiers, Burlington, CT (US); A. Jon Goldberg, West Hartford, CT (US)

(73) Assignee: University of Connecticut, Farmington, CT (US)

( * ) Notice: Subject to any disclaimer, the term of this patent is extended or adjusted under 35 U.S.C. 154(b) by 97 days.

(21) Appl. No.: 09/645,951

(22) Filed: Aug. 25, 2000

Related U.S. Application Data (60) Provisional application No. 60/151,003, filed on Aug. 27, 1999.

(51) Int. Cl.[7] .............................................. A61C 13/08
(52) U.S. Cl. .................................... 433/212.1; 433/180
(58) Field of Search ................................ 433/173, 180, 433/181, 215, 202.1, 212.1

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,751,399 A | 8/1973 | Lee | |
| 3,926,906 A | 12/1975 | Lee, II et al. | |
| 4,457,714 A | 7/1984 | Klein | |
| 4,544,359 A | 10/1985 | Waknine | |
| 4,547,531 A | 10/1985 | Waknine | |
| 4,717,341 A | 1/1988 | Goldberg et al. | |
| 4,735,571 A | 4/1988 | Salvo | |
| 4,775,320 A | 10/1988 | Marshall | |
| 4,877,400 A | 10/1989 | Holsclaw | |
| 4,894,012 A | 1/1990 | Goldberg et al. | |
| 5,098,304 A | 3/1992 | Scharf | |
| 5,110,513 A | * 5/1992 | Puvilland | 433/228.1 |
| 5,120,224 A | 6/1992 | Golub | |
| 5,276,068 A | 1/1994 | Waknine | |
| 5,360,482 A | 11/1994 | Belvedere | |
| 5,444,104 A | 8/1995 | Waknine | |
| 5,545,039 A | 8/1996 | Mushabac | |
| 5,564,929 A | 10/1996 | Alpert | |
| 5,684,103 A | 11/1997 | Jia et al. | |

(List continued on next page.)

FOREIGN PATENT DOCUMENTS

WO    WO 94/08783    4/1994

OTHER PUBLICATIONS

Meiers, J.C., Freilich, M.A., Chairside prefabricated fiber–reinforced resin composite fixed partial dentures. Quintessence International, 2001, 99–104. vol. 32, No. (2).

Primary Examiner—Ralph A. Lewis
(74) Attorney, Agent, or Firm—Ann M. Knab (57) ABSTRACT

Ready-to-use preshaped, prefabricated cured components and hybrid components are prepared in a variety of shapes and sizes to be used in the fabrication of dental appliances. Preferably the structural components are fabricated of a fiber-reinforced composite material comprising fibers impregnated with a polymeric matrix. The polymeric matrix is partially or fully cured to the point of sufficient hardness to provide a ready-to-use structural component for use in the fabrication of dental appliances such as The component of claim 1 wherein the dental appliance system is selected from the group consisting of orthodontic retainers, bridges, space maintainers, tooth replacement appliances, splints, crowns, partial crowns, dentures, posts, teeth, jackets, inlays, onlays, facings, veneers, facets, implants, cylinders, abutments, pins and connectors. Hybrid components comprise two or more sections whereby at least one section is cured and at least one section is uncured to facilitate indirect and direct application of the component in the fabrication of a dental restoration.

59 Claims, 5 Drawing Sheets

U.S. PATENT DOCUMENTS

| | | | |
|---|---|---|---|
| 5,772,438 A | 6/1998 | Deom | |
| 5,797,748 A | 8/1998 | Reynaud | |
| 5,816,816 A | 10/1998 | Scharf | |
| 5,846,640 A | 12/1998 | Vallittu | |
| 5,919,044 A * | 7/1999 | Sicurelli, Jr. et al. | 433/220 |
| 5,921,778 A * | 7/1999 | Karmaker et al. | 433/215 |
| 5,984,682 A * | 11/1999 | Carlson | 433/180 |
| 6,013,694 A | 1/2000 | Jia et al. | |
| 6,030,220 A * | 2/2000 | Karmaker et al. | 433/215 |
| 6,039,569 A | 3/2000 | Prasad et al. | |
| 6,186,790 B1 * | 2/2001 | Karmaker et al. | 433/215 |
| 6,200,136 B1 * | 3/2001 | Prasad et al. | 433/180 |
| 6,267,597 B1 * | 7/2001 | Kim | 433/224 |
| 6,287,122 B1 * | 9/2001 | Seeram et al. | 433/220 |
| 6,287,490 B2 * | 9/2001 | Rheinberger et al. | 433/215 |
| 6,334,775 B2 * | 1/2002 | Xu et al. | 433/228.1 |
| 6,345,984 B2 * | 2/2002 | Karmaker et al. | 433/173 |
| 6,362,250 B1 * | 3/2002 | Karmaker et al. | 523/116 |

* cited by examiner

PREFABRICATED COMPONENTS FOR DENTAL APPLIANCES

CROSS-REFERENCE TO RELATED APPLICATIONS

This application claims priority to provisional application serial No. 60/151,003 filed Aug. 27, 1999 entitled FABRICATION OF PRE-MADE COMPOSITE/FIBER-REINFORCED COMPOSITE PONTICS.

TECHNICAL FIELD

The present invention relates generally to dental appliances and restorations and particularly to prefabricated components for use in dental appliances and restorations and methods of manufacture thereof and more particularly to prefabricated hybrid components for use in dental appliances and restorations.

BACKGROUND OF THE INVENTION

Dental appliances and restorations such as bridges, crowns, dentures and the like may be used to restore a missing tooth and retain natural teeth in position and prevent migration subsequent to orthodontic treatment. Structural components used in these appliances often include wires, bars, posts, shells, beams, clasps and other shapes. The shape of the structural components may vary depending upon the requirements of the appliance.

The manufacture of frameworks for bridges using current techniques can be time consuming and labor intensive. Some techniques may involve taking uncured fiber-reinforced composite material and forming uncured strips of the fiber-reinforced composite material into a bridge framework upon a dental cast. The procedure can be an involved and complex process depending upon the final shape desired. Moreover, dental technicians and practitioners may use less than the optimum amount of fiber for reinforcement when preparing the dental framework in order to reduce the cost which may lead to low strength and therefore potential fracture of the final product. Furthermore, the complexity of the dental appliance may require a certain dexterity to achieve optimal properties that may not be achievable by some technicians and practitioners. The use of metals, alloys and ceramics which exhibit high flexural strengths such as 300 MPa and higher reduces light transmission and thus affects the aesthetic appearance.

There remains a need to simplify the process of fabricating dental appliances to reduce time and labor involved in the preparation process and to provide appliances having optimum properties. It is desirable to reduce the risk of contamination during the fabrication of dental appliances. It is desirable to maintain strength of dental appliances without sacrificing aesthetic and light transmitting properties. It is beneficial to faciliate the dental applicance fabrication process in the dental laboratory and at the dentist office.

SUMMARY OF THE INVENTION

These and other objects and advantages are accomplished by the present invention wherein preshaped, prefabricated cured components are prepared in a variety of shapes and sizes to be used in the fabrication of dental appliances. Preferably the components are fabricated of a fiber-reinforced composite material comprising fibers impregnated with a polymeric matrix. After impregnation of a fibrous material with a polymeric matrix, the resultant fiber-reinforced composite material is shaped and is partially or fully cured to the point of sufficient hardness to provide a component for use in the fabrication of dental appliances including but not limited to orthodontic retainers, bridges, space maintainers, tooth replacement appliances, dentures, posts, crowns, posts, jackets, inlays, onlays, facings, veneers, facets, implants, abutments, splints, partial crowns, teeth, cylinders, pins, and connectors.

In one embodiment herein, the components are in the shape of a structure for immediate use in the fabrication of a dental appliance. The structural components are formed into any known shapes useful in the fabrication of a dental appliance or restoration. Preferably, the structural components are in the shape of bars, rods or pontics. The pontics have interproximal extensions and may be single-unit or multiple-unit useful in the fabrication of frameworks for bridges. The structural components may be "ready-to-use" for immediate use in the fabrication of a dental appliance or restoration or may be further modified, for example by cutting, carving, etching, abrading or grinding prior to using in the fabrication of a dental appliance or restoration.

In another embodiment herein, the components are formed into pieces or blocks of fiber-reinforced composite material. The blocks of material are useful in making a variety of shapes and sizes and may be modified by a variety of methods including but not limited to machining, carving, cutting, grinding, etching or abrading.

The bars, rods, pontics and blocks may be of any cross-sectional configuration effective to provide strength and stiffness to the finished dental appliance.

In yet another embodiment herein, preshaped, prefabricated hybrid components are provided wherein at least one section of the component is cured and at least one section of the component is uncured. The component is a "hybrid" component due to the combination of a cured or partially cured section or sections with an uncured or slightly partially cured section or sections. The hybrid components are useful in the fabrication of dental appliances or restorations whereby the uncured or slightly partially cured sections are cured at the point of insertion in the patient's mouth providing ease of application due to the flexibility and adaptability of the uncured/slightly partially cured sections and optimum bonding of the uncured/slightly partially cured component to the patient's existing teeth and/or to other cured, partially cured or uncured components. The cured/partially sections of the hybrid components are substantially hard and are not amenable to bending, but may be modified by a variety of methods used on hard components without disrupting the structural integrity of the component including machining, carving, cutting, grinding, etching, and abrading. The uncured/slightly partially cured sections of the hybrid components are very soft and flexible and may be modified by a variety of methods including forming, shaping, contouring, adjusting, and etching.

In one method of manufacture, the components are made after the impregnation of the fibers with a polymeric matrix. After impregnation of the fibers, the resultant composite material is formed into, for example, a long bar and cured or polymerized to a hardness whereby the bar may be cut and/or machined without deforming the structural integrity of the bar. The bar is preferably cut into short segments and is ready for use in the fabrication of dental appliances. The bars may be used as is or may be further modified by cutting, grinding, machining, and the like to provide a specifically shaped or customized component. The component may further be veneered with a composite material such as a particulate-filled composite to develop clinically acceptable anatomy.

In another method of manufacture, prefabricated preshaped hybrid components are manufactured using special molds to permit curing in limited sections of the components. Filled (fiber, particulate or filler or a reinforcing component) composite material is inserted into a section of a lower mold piece or half to be cured. The material is cured or partially cured and more composite material, preferably, fiber-reinforced composite material is inserted into various sections of the mold. The fiber-reinforced composite material is not cured. Thereafter, additional composite material (fiber, particulate, filler or other reinforcing component) is placed on the section of material that was originally cured or partially cured. The lower mold piece is then covered with an upper mold piece or pieces to form and shape the material therein to the desired shape. The upper mold pieces covering the sections of the mold having composite material to be cured are removed leaving those upper mold sections covering the composite material to remain uncured. The uncovered mold section having composite to be cured is subsequently light cured. The resultant component is removed from the mold pieces and the uncured sections of the component are covered with a protective sleeve to prevent contamination and curing until the component is to be used in the fabrication of a dental restoration or appliance.

BRIEF DESCRIPTION OF THE DRAWINGS

Features of the present invention are disclosed in the accompanying drawings, wherein similar reference characters denote similar elements throughout the several views, and wherein.

DETAILED DESCRIPTION

The prefabricated components in accordance with the present invention are formed from a composite material comprising a polymeric matrix and a filler or reinforcing agent within the matrix. Preferably, the composite is a fiber-reinforced composite comprising a polymeric matrix and reinforcing fibers within the matrix. Alternatively, a section or layer of the component may comprise particulate filled composite material alone, or in combination with the fiber-reinforced composite material. The fibers are embedded in the matrix manually or mechanically by a variety of techniques including, but not limited to matched die processes, autoclave molding, resin injection molding (RIM), sheet, dough and bulk molding, press molding, injection molding, reaction injection molding, resin transfer molding (RTM), compression molding, open molding, extrusion, pultrusion and filament winding. U.S. Pat. Nos. 4,717,341 and 4,894,012 to Goldberg et al. show methods of impregnation and are hereby incorporated by reference. Preferably the fiber-reinforced polymeric matrix is formed using the pultrusion or filament winding technique.

The polymeric matrix element of the composite materials is selected from those known in the art of dental materials, including but not being limited to polyamides, polyesters, polyolefins, polyimides, polyarylates, polyurethanes, vinyl esters or epoxy-based materials. Other polymeric matrices include styrenes, stryrene acrylonitriles, ABS polymers, polysulfones, polyacetals, polycarbonates, polyphenylene sulfides, and the like.

Preferred polymeric materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BISGMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), polycarbonate dimethacrylate (hereinafter abbreviated "PCDMA") and ethoxylated bisphenol A dimethacrylate (hereinafter abbreviated "EBPADMA") are also commonly-used principal polymers suitable for use in the present invention.

The polymer matrix typically includes polymerization initiators, polymerization accelerators, ultraviolet light absorbers, anti-oxidants, and other additives well known in the art. The polymer matrices may be visible light curable, self-curing, dual curing, and vacuum, heat, and pressure curable compositions as well as any combination thereof. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, in addition to the monomeric components, a heat cure initiator such as benzoyl peroxide, 1,1'-azobis(cyclohexanecarbo-nitrile), or other free radical initiators. The preferred polymeric matrix is a curable matrix, wherein light cure effects partial cure of the matrix, and final curing is by heat under controlled atmosphere.

Suitable fillers for the particulate filled composite are those capable of being covalently bonded to the polymeric matrix itself or to a coupling agent that is covalently bonded to both. Examples of suitable filling materials include but are not limited to those known in the art such as silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania. Particularly suitable fillers for dental filling-type materials prepared in accordance with this invention are those having a particle size ranging from about 0.1–5.0 microns with a silicate colloid of 0.001 to about 0.07 microns and may be prepared by a series of milling steps comprising wet milling in an aqueous medium, surface etch milling and dry or wet silanation. Some of the aforementioned inorganic filling materials are disclosed in commonly-assigned U.S. Pat. No. 4,544,359 and No. 4,547,531 to Waknine, the pertinent portions of which are incorporated herein by reference.

The polymeric matrix of the fiber-reinforced composite material may further comprise at least one filler as listed above, in combination with the fiber component, known in the art and used in dental restorative materials, the amount of such filler being determined by the specific use of the fiber-reinforced composite. Generally, no or relatively little additional filler is present in the polymeric matrix, i.e., up to thirty percent by weight of the composite.

The reinforcing fiber element of the composite preferably comprises glass, carbon, graphite, polyaramid, or other fibers known in the art, such as polyesters, polyamides, and other natural and synthetic materials compatible with the polymeric matrix. Some of the aforementioned fibrous materials are disclosed in commonly assigned copending U.S. patent application Ser. Nos. 08/907,177, 09/059,492, 60/055,590, 08/951,414 and U.S. Pat. Nos. 4,717,341 and 4,894,012 all which are incorporated herein by reference. The fibers may further be treated, for example, chemically or mechanically etched and/or silanized, to enhance the bond between the fibers and the polymeric matrix. The fibers preferably take the form of long, continuous filaments, although the filaments may be as short as 0.1 to 4 millimeters. Shorter fibers of uniform or random length might also be employed. Preferably, the fibers are at least partially aligned and oriented along the longitudinal dimensions of the wire. However, depending on the end use of the composite material, the fibers may also be otherwise oriented, including being normal or perpendicular to that dimension. The fibers may also be randomly dispersed. The fibrous element may optionally take the form of a fabric. Fabric may be of the woven or non-woven type and is preferably preimpregnated with a polymeric material as set forth above. Examples of suitable woven fabric materials include but are not limited to those known in the art such as E glass and S glass fabrics and reinforcement fabrics sold by NFGS Inc. of New Hampshire under the style numbers 6522 and 7581. One preferred non-woven fabric material is available under the name Glass Tissue (20103A) from Technical Fibre Products Ltd. of Slate Hill, N.Y. The fibrous component may be present in the fiber reinforced composite material in the range from about 20% to about 85%, and more preferably between about 30% to about 65% by weight.

Fabric may also be combined with the fiber-reinforced composite material to produce a high strength appliance. Fabric may be of the woven or non-woven type as discussed above and is preferably preimpregnated with a polymeric material. Suitable polymeric materials are those listed above as polymeric matrix materials.

In accordance with one embodiment herein, the fiber-reinforced polymeric composite material is preformed into structural components to provide ready-to-use units for use in the fabrication of dental appliances. The structural components are formed into any known shape(s) useful in the fabrication of a dental appliance or restoration. Preferably, the structural components are in the shape of bars, rods or pontics. The pontics have interproximal extensions and may be single unit or multiple unit useful in the fabrication of frameworks for bridges. The bars, rods and pontics may be straight or curved depending on the end use. The structural components may be "ready-to-use" for immediate use in the fabrication of a dental appliance or restoration or may be further modified, for example by cutting, carving or grinding prior to using in the fabrication of a dental appliance or restoration.

FIG. 1 shows various shapes of bars formed in accordance with the present invention. FIGS. 1A through 1D depict bars of square 10, circular 12, rectangular 14 and triangular 16 cross-section, respectively. Structural components in the form of bars are typically used in the manufacture of dental bridges or posts. If posts are desired, the cross-sectional dimension of the post must be narrow enough to fit within the root canal.

Figure 5:
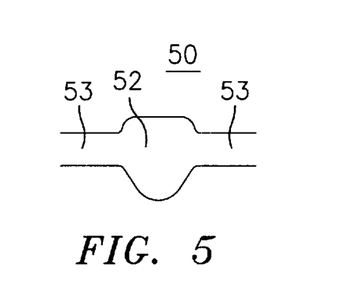
FIG. 5 is a front elevational view of a single unit pontic formed using a mold in FIG. 4.

More complicated shapes of preformed structural components may be formed from the structural bars either manually or mechanically by carving, cutting, grinding, machining or using other similar means. In instances where the components comprise uncured or partially cured sections, those sections may be modified by forming, shaping and contouring by hand or by using hand instruments. The complicated shapes may include pontics of varying lengths and shapes as noted above and as shown in FIGS. 2, 3 and 5, but are not limited to the specific shapes shown. Alternatively, the complicated shapes may be formed by pressing composite material into molds and fully or partially curing into a hardness sufficient to withstand cutting, carving or machining. In a preferred embodiment, preformed structural bars are placed within a series of molds and composite material is filled into the cavities surrounding the bars to form a single unit pontic 50 as shown in FIG. 5.

Figure 1A:
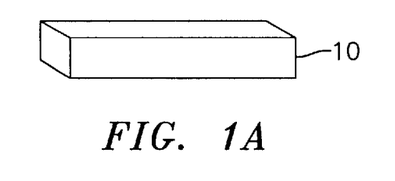
FIG. 1 is a perspective view of bars of different shapes that may be formed in accordance with the present invention.
Figure 1B:
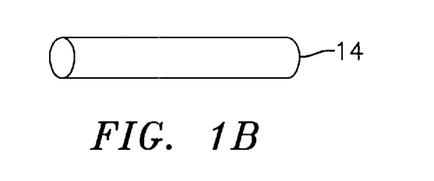
Figure 1C:
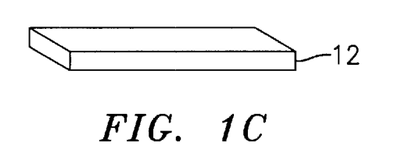
Figure 1D:
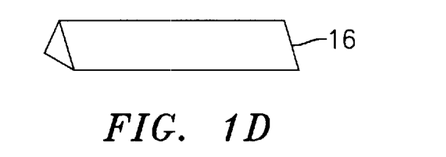
Figure 2:
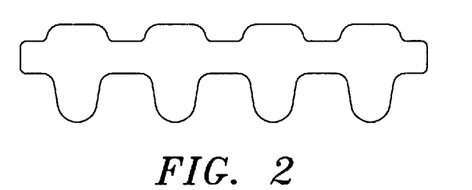
FIG. 2 is a front elevational view of a multi-unit pontic formed in accordance with the present invention.
Figure 3:
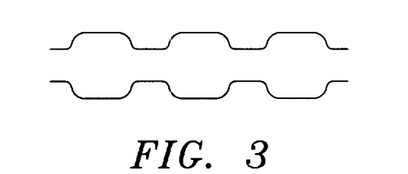
FIG. 3 is a top plan view of a multi-unit pontic formed in accordance with the present invention.

FIG. 2 shows a multiple unit pontic 20 that may be used in the preparation of an anterior bridge. FIG. 3 displays a multiple unit pontic 30 that could be used in the preparation of a bridge.

Figure 4:
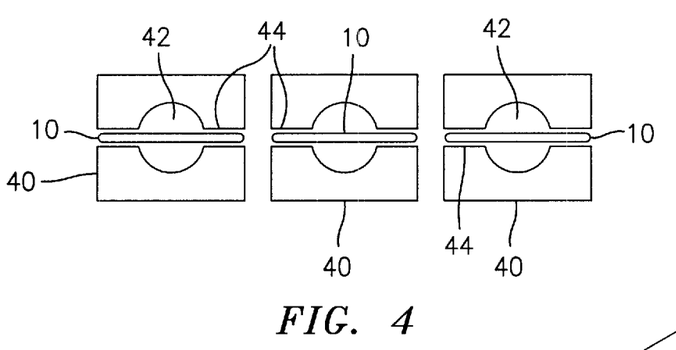
FIG. 4 is a top plan view of a series of molds used to fabricate single unit pontics in accordance with the present invention.
Figure 6:
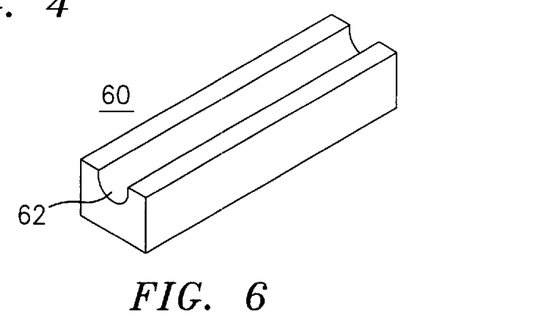
FIG. 6 is a side elevational view of a mold used to fabricate long bars in accordance with the present invention.

FIG. 4 depicts a series of molds 40 having cavities 42 therein connected to laterally extending thin sections 44. FIG. 6 shows a single mold 60 having a longitudinally extending cavity 62 used to fabricate a long bar that may be cut into smaller sections after it has cured. In accordance with one process of the present invention, one or more layers of filled composite material may be poured into cavities 42. Preferred composite materials include Flow-It composite and Lute-It composite available from Jeneric/Pentron Inc., Wallingford, Conn. One or more layers of pre-impregnated woven or nonwoven fabric may be placed on the composite layer(s). Alternately, the fabric may be first placed in the cavities 42 and composite material may be deposited thereover. After the composite and/or fabric is provided in cavities 42, preformed structural bars 10 may be placed within mold 40 as shown. More composite material may be used to fill any voids in cavities 42. The material is cured to form a structural component in the shape of a single unit pontic 50 (FIG. 5) having a central pontic section 52 and laterally extending arms 53. Preferably, the molded component is cured to a sufficient hardness whereby it may be machined or carved to a desired final shape by the technician or dentist during fabrication of the dental appliance. The molded component may be partially cured at the time of fabrication and the curing can be completed at the time of fabrication of the dental appliance or the molded component may be fully cured at the time of manufacture thereof. Mold 60 may be used in a similar fashion to molds 40 to prepare a long bar that may cut into smaller sections after it has cured.

In another embodiment herein, the components are formed into pieces or blocks of fiber-reinforced composite material. The blocks of material may be provided in a variety of shapes and sizes and may be modified by a variety of methods including but not limited to machining, carving, cutting, grinding, abrading or etching.

Figure 7:
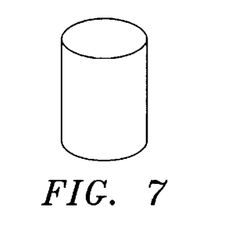
FIG. 7 is a perspective view of a cylindrical block formed in accordance with the present invention.
Figure 8:
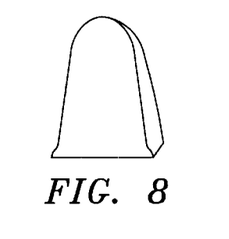
FIG. 8 is a perspective view of a tooth machined out of the block shown in FIG. 7.
Figure 9:
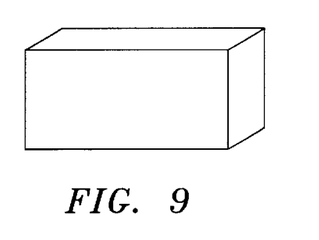
FIG. 9 is a perspective view of a rectangular block formed in accordance with the present invention.
Figure 10:
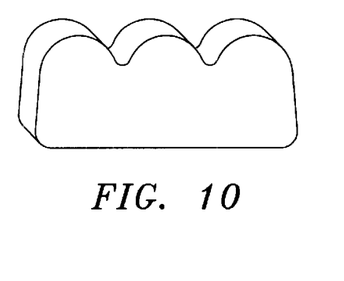
FIG. 10 is a perspective view of a bridge machined out of the block shown in FIG. 9.
Figure 11:
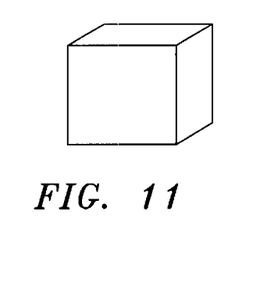
FIG. 11 is a perspective view of a square block formed in accordance with the present invention.
Figure 12:
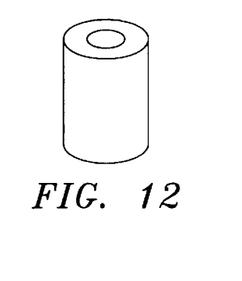
FIG. 12 is a perspective view of a cylinder machined out of the block shown in FIG. 11.

FIGS. 7, 9 and 11 depict blocks formed in accordance with the present invention. FIG. 7 shows a cylindrical block, FIG. 9 shows a rectangular block and FIG. 11 shows a square block. FIG. 8 depicts a tooth which has been machined from the block shown in FIG. 7. FIG. 10 shows a bridge machined from the block in FIG. 9. FIG. 12 shows a cylinder for use is an implant machined from the block in FIG. 11.

Figure 13:
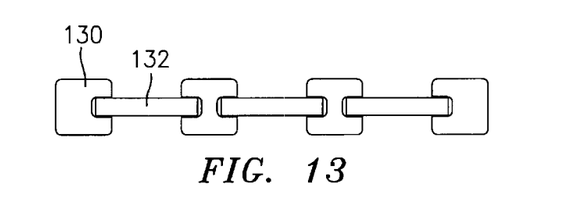
FIG. 13 is a perspective view of a partial implant system formed from structural components of the present invention.

The cylinder shown in FIG. 12 can be used in combination with prefabricated bars of the present invention or may be used with uncured fiber-reinforced composite material such as Fiberkor® available from Jeneric/Pentron Inc., Wallingford, Conn. An implant may be manufactured with one or all of its components fabricated from the structural components of the present invention including but not limited to the abutments, cylinders and framework. The resulting implant components provide good shock absorbancy. Preferably the implant components are machined out of blocks fabricated in accordance with the present invention. The machined blocks may include retentive designs on the eternal service for proper linkage to create multi-unit bridges or to reinforce bonding to the overlay composite materials. The implant superstructure may additionally include pontic components for proper support of the overlay material. FIG. 13 shows a partial implant system wherein cylinders 130 and bars 132 are disposed therebetween to form the superstructure. Cylinders 130 are preferably machined from blocks made in accordance with the present invention. Bars 132 are likewise manufactured in accordance with the present invention.

Figure 14:
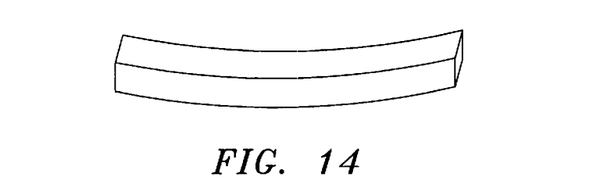
FIG. 14 is a perspective view of a curved rectangular block formed in accordance with the present invention.
Figure 15:
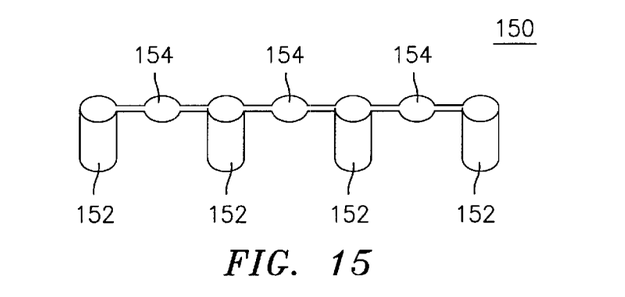
FIG. 15 is a perspective view of an implant superstructure machined out of the block shown in FIG. 14.

FIG. 14 shows a curved rectangular block formed in accordance with the present invention. FIG. 15 shows an implant superstructure 150 which has been machined from the block shown in FIG. 14. Superstructure 150 comprises cylinders 152 interconnected with pontic sections 154.

In accordance with the method of the present invention, the components may be manufactured on line as part of the fiber impregnation process or may be molded into shapes after the impregnation process. In a preferred embodiment of the invention, components in the form of, for example, bars or blocks may be manufactured following the process of fiber impregnation with a matrix material. The bars or blocks are preferably formed under pressure and undergo either full or partial polymerization to impart specific properties for specific applications. Long, continuous bars or blocks may be molded and cured to a hardness sufficient to withstand cutting, carving or machining and subsequently cut into the desired lengths at the time of manufacture or at some point thereafter. The cross-section of the structural components may be square, rectangular, triangular, rhomboidal, ovoidal, tapered, cylindrical, or of any other cross-sectional configuration effective to provide strength and stiffness to the finished dental appliance. The dimensions may be of varying lengths, widths and heights and the shades thereof may be of any shade suitable for dental materials. Coloring agents known in the art may be added to the polymeric matrix material prior to curing.

The components may be used as frameworks or understructures for crowns, bridges, implant abutment cylinders, implant superstructures and the like. The framework/understructure can be made from the structural components in a variety of ways. The method of fabrication may be manual or automated. In the manual method, a technician can select a component of, for example, rectangular shape. The technician cuts the block to proper dimension and size and carves out or shapes the desired anatomical features using standard laboratory tools.

To perform the procedure by automated or mechanical means, an apparatus such as a CAD/CAMming machine is used to automatically shape the structural component into the form or contour desired. The component is preferably in the form of a block (also known as a blank) for CAD/CAMming purposes. The technicians and/or practitioners collect three dimensional data regarding the final desired shape of the dental appliance or restoration and machine or mill the block or blank to achieve the final desired shape. The data may be collected from actual teeth, implants, etc. or from models or prefabricated frameworks (of wax, duralay, etc.) prepared on teeth or stone models or from an impression taken of the tooth or teeth to be corrected by using a scanning device such as the Pro-Scan™ device available from IntraTech in Irving, Tex. The data may be used as is or may be modified using computer software. Based on the data, the blank is machined via CAM to a three-dimensional dental appliance or material. The CAD/CAM process may be performed at one location or the CAD data may be transferred via modem or electronic transmission to another location where computer assisted machining or milling is performed. The machined part may be further modified or treated with for example, a surface treatment such as abrasion, etching, or silanation, or with a special bonding agent. Additionally, the machined part can be joined with other preimpregnated fiber-reinforced materials prior to being overlaid with a coating or veneer. The veneer may be a particulate-filled composite material such as commerically available Sculpture® material available from Jeneric/Pentron Inc., Wallingford, Conn. and is preferably applied to the machined or manually carved part to provide the final anatomy. The finished appliance or restoration can either be bonded or mechanically anchored. Bonding is the preferred fastening means.

The prefabricated, preshaped fully or partially cured components of the present invention can substantially eliminate operator induced errors, greatly save time and enhance overall properties and longevity of final restorations. For implant restorations, replacement of the rigid (high modulus) metal components with a lower modulus material of the fiber-reinforced composite structural components, improves shock absorption.

In a preferred embodiment herein, the preshaped, prefabricated components are one-piece hybrid components comprising two or more sections of composite material comprising a polymeric matrix and a filler or reinforcing agent or a combination thereof within the matrix. As stated above, the components may comprise layers of composite material (filler, particulate, fiber, fabric or combinations thereof in a polymeric matrix). For example, a component may comprise a layer of particulate filled material, a layer of fiber-reinforced material and a layer of fabric impregnated material or one or more layers of fiber-reinforced material or any combination of composite materials. At least one of the sections of the component is cured and at least one of the sections of the component is uncured. The component is a "hybrid" component due to the combination of a cured section or sections with an uncured or slightly partially cured section or sections. The hybrid components are ready-to-use components and are useful in the fabrication of dental appliances or restorations whereby the uncured or slightly partially cured sections are cured at the point of insertion in the patient's mouth providing ease of application due to the flexibility and adaptability of the uncured sections and optimum bonding of the uncured or slightly partially cured component to the patient's existing teeth or to other components of the appliance or restoration. Preferably, the hybrid components are in the shape of a pontic although other shapes, sizes and cross-sections such as those mentioned above for the cured components are also acceptable.

Figure 16:
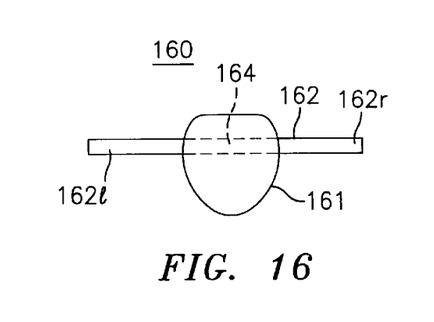
FIG. 16 is a front elevational view of a single unit hybrid pontic in accordance with the present invention.

Reference is made to FIG. 16 showing a preferred hybrid component, single unit pontic 160, having a middle pontic section 161 and interproximal extensions 162 (right extension 162r and left extension 162l). Middle section 161 comprises a composite material (polymeric matrix material with filler, fiber, fabric or particulate therein as set forth above) such as a filled composite material such as commercially available Sculpture® composite resin available from Jeneric/Pentron Inc., Wallingford, Conn. The composite material in middle section 161 is cured or partially cured to sufficient hardness to withstand cutting, carving, grinding or machining. Sections 162l and 162r comprise fiber-reinforced composite material such as FibreKor® material also available from Jeneric/Pentron Inc. Partial curing of material in section 161 prior to positioning fiber-reinforced composite material in sections 162l and 162r and across section 161 allows better bonding of the composite material in section 161 with the fiber-reinforced composite material placed across section 161 and into sections 162l and 162r at the point of contact between the different materials. The fiber-reinforced composite material is uncured or only slightly partially cured in the proximal extensions 162l and 162r. In the fabrication of pontic 160, the fiber-reinforced composite material is positioned across middle section 161 as noted by the dotted line section 164 in middle section 161. Section 164 may be cured fully or partially in middle section 161 or left uncured until more composite material is applied over section 164 which is then cured partially or fully, sufficiently to a hardness to a point of being able to be machined, carved or ground. In this way, fiber-reinforced composite material forming the interproximal extensions is sandwiched in the middle section of the component thereby sufficiently securing proximal extensions 162 to middle section 161. Pontic 160 is a hybrid component in that it has sections having different degrees of polymerization, i.e., at least one section (164) is cured and at least one section (sections 162l and 162r) is/are uncured.

Figure 17:
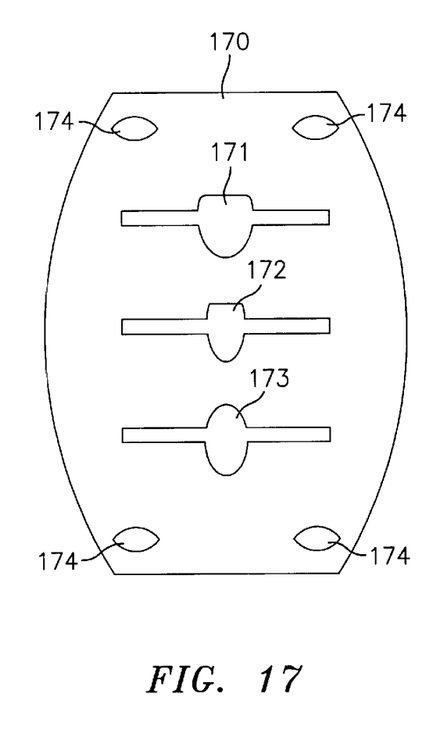
FIG. 17 is a top plan view of a lower mold section for use in the manufacture of a hybrid pontic.
Figure 18:
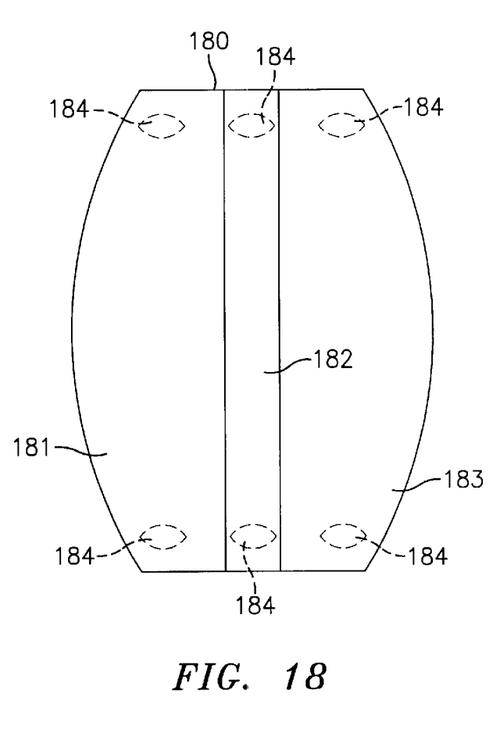
FIG. 18 is a top plan view of an upper mold section for use in the manufacture of a hybrid pontic.
Figure 24:
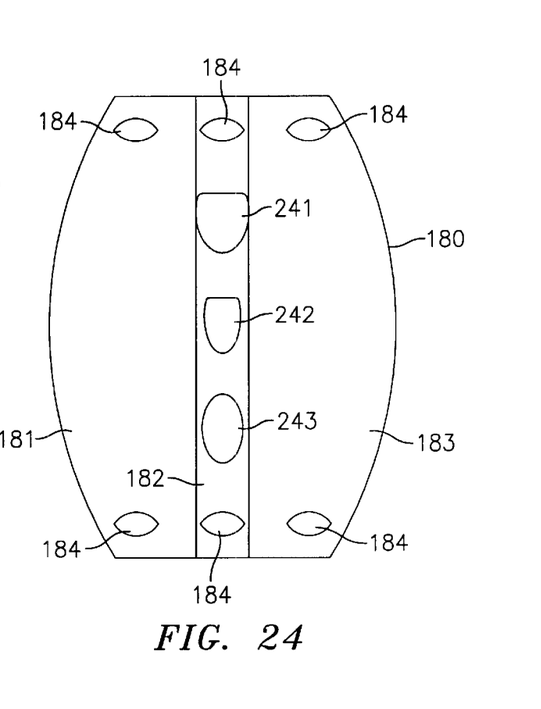
FIG. 24 is a top plan view of the interior of the upper mold section of FIG. 18.

FIG. 17 is an example of a lower mold half 170 for the fabrication of various pontic shapes such as those shown in mold shape depressions 171, 172 and 173. All mold sections may be fabricated of any of the known mold materials in the art such as vinylsiloxane impression materials. One preferred material is Correct Quick® vinylpolysiloxane from Jeneric/Pentron Inc. FIG. 18 shows an upper mold half 180 for covering lower mold section 170. Mold 180 is divided into three sections, 181, 182 and 183 for individually covering the left side, the middle and the right side, respectively, of lower mold 170. Lower mold half 170 contains indentations or protrusions or similar retaining means 174 which correspond to protrusions or indentations or similar retaining means 184 in upper mold half 180 to retain the mold halves in proper position with respect to one another. FIG. 24 shows the interior of mold 180 whereby section 182 comprises depressions therein to shape the middle section of the pontic. Depressions for the interproximal extensions are not included in mold sections 181 and 183, but may be included, if desired.

Figure 19:
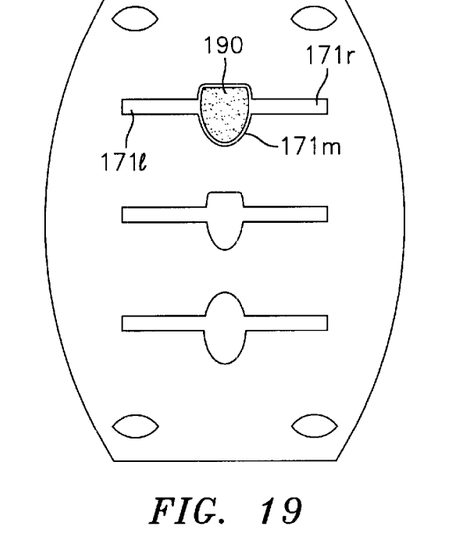
FIG. 19 is a top plan view of a lower mold section showing a processing step in the manufacture of a hybrid pontic.
Figure 20:
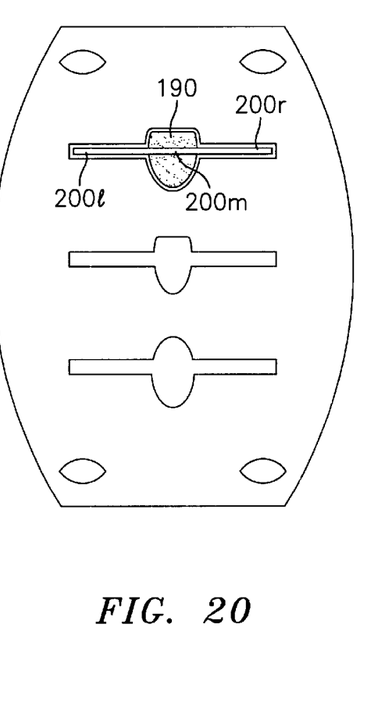
FIG. 20 is a top plan view of a lower mold section showing a processing step in the manufacture of a hybrid pontic.
Figure 21:
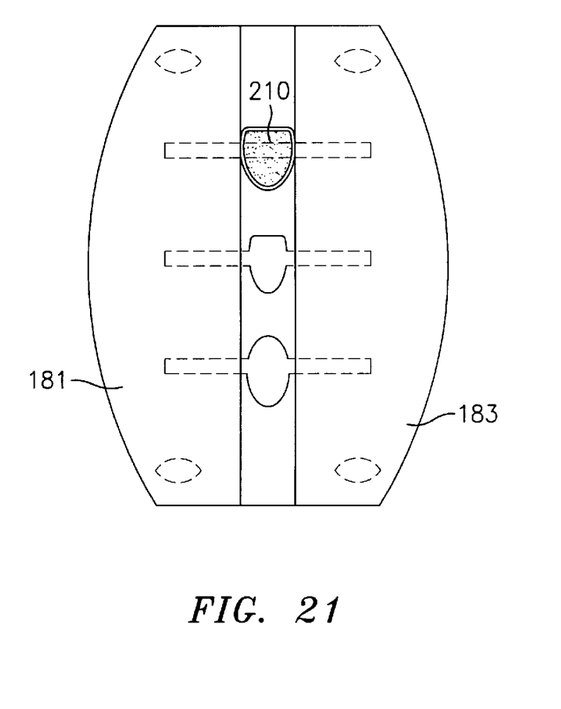
FIG. 21 is a top plan view of mold pieces showing a processing step in the manufacture of a hybrid pontic.

FIGS. 19–21 illustrate process steps occurring during the manufacturing process of a pontic. FIG. 19 shows lower mold half 170 with filled composite material 190 inserted in middle section 171m. No material is inserted in interproxmal extension sections 171l and 171r. Material 190 in section 171 is subsequently light-cured. Preferably, material 190 is only partially cured at this point so that it may better bond to the fiber-reinforced composite material which is positioned over material 190. FIG. 20 shows fiber-reinforced composite material 200 inserted in interproxmal extension sections 171l and 171r. Fiber-reinforced composite material 200 is inserted across section 171m on material 190. Material 200 is not cured. Thereafter, more filled composite material 210 may be added to middle section 171 over that section of uncured fiber-reinforced composite material 200m which is located in middle section 171 and cured material 190 which is located under material 200m. Mold sections 181, 182 and 183 of mold half 180 are placed on the respective positions of lower mold half 170 to shape the component materials therein. Thereafter, mold section 182 is removed and mold sections 181 and 183 remain as shown in FIG. 21 to protect the left and right sides of uncured fiber-reinforced composite material 200. Material 210 and material 200m (and material 190 if not originally fully cured are subsequently light cured). Fiber-reinforced composite material 200l and 200r located in interproximal sections 171l and 171r remains uncured. The hybrid pontic is removed from the mold and uncured fiber-reinforced composite material sections 200l and 200r of the ready-to-use pontic are thereafter covered with a dark or opaque protective cover such as dark plastic bags or dark mylar-type material sleeves to prevent the uncured sections from curing and to prevent contamination thereof prior to use in the fabrication of a dental restoration or appliance. Additionally, aluminum foil may be wrapped over the mylar or similar material for further protection against polymerization and contamination. It is important that the protective material is dark or opaque to prevent polymerization and is also non-sticky to prevent adherence of the polymeric resin material.

Preferably, a thin sleeve of darkened acetate is used to cover the uncured interproximal extensions.

Figure 22:
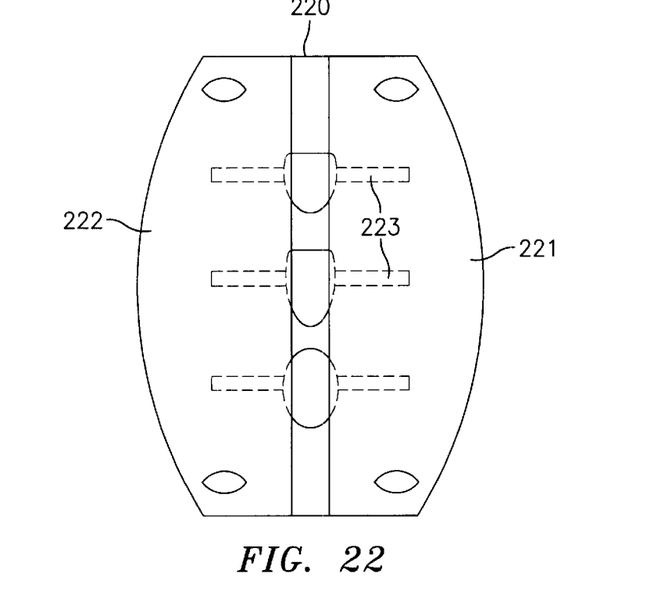
FIG. 22 is a top plan view of a mold pieces for use in the manufacture of a hybrid pontic.
Figure 23:
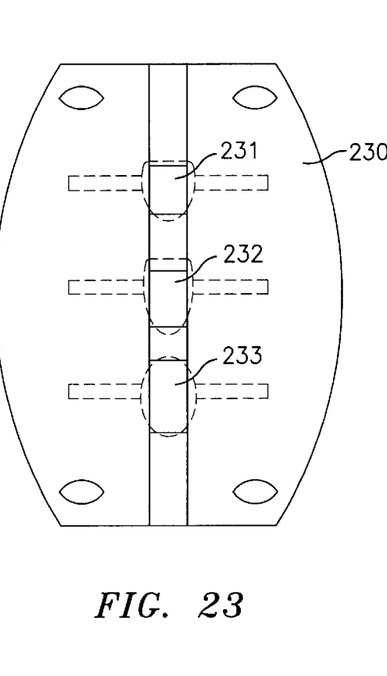
FIG. 23 is a top plan view of alternate mold pieces for use in the manufacture of a hybrid pontic.

In accordance with alternate mold embodiments herein, reference is made to FIGS. 22 and 23. FIG. 22 shows lower mold component 220 and upper mold components 221 and 222. Mold components 221 and 222 cover the perimeter of the sides of the middle pontic sections of the mold such that the sides of the middle section are protected during curing and remain unpolymerized along with wings or interproximal extensions 223. As shown in FIG. 22, the dotted-line sections will be protected during curing. In this way, when the component is to be used in the fabrication of a restoration or appliance, the perimeter of the middle pontic section along the sides in addition to the interproximal extensions will readily bond to the abutment teeth or other component to which it is to be attached. Similarly, FIG. 23 refers to yet a more protective mold cover 230 which contains openings 231, 232 and 233 to allow for the central section of the pontic section to be cured. The perimeter of the pontic section remains uncured for optimum bonding at the time of manufacture of the dental restoration. Alternate molds may be used depending on the area to be cured and uncured. For example, since it is not be necessary to bond the tip of the tooth to anything, the tip may be left uncovered during the polymerization process of the component.

As an example of a hybrid component, a hybrid pontic may be used to fabricate a bridge or similar appliance in the laboratory or may be used in the dental office (chairside) for immediate insertion into the patient's mouth. If used in the laboratory, the dental laboratory technician removes the prefabricated fiber-reinforced composite strip/filled composite pontic from a darkened plastic bag and places the pontic into the edentulous area of an improved plaster (stone) cast made from an alginate impression of the mouth. The correct shade of composite is added to the pontic as the interproximal lingual fiber-reinforced composite wings remain covered with their protective sleeves to remain unpolymerized or uncured. The laboratory sends the dentist the full-contoured, correctly shaded pontic with unpolymerized fiber-reinforced composite extending from the proximal surfaces of the pontic. At chairside, after rubber dam placement, acid etching of the abutment teeth and the placement of unfilled resin over the etched enamel, the dentist places the pontic into the edentulous area and bonds it into place. This occurs stepwise (one proximal, then the next proximal, then the protective sleeves are removed from the fiber-reinforced composite wings on the lingual) using a low-viscosity hybrid composite.

The dentist then adds composite to cover the interproximal fiber-reinforced composite strips located lingually or facially on the abutment teeth in the mouth and adjusts the occlusion if necessary, completing the single-tooth replacement prosthesis.

Alternatively, as another example, the hybrid pontic is used directly by the dentist to prepare a restoration or appliance for direct insertion in the patient's mouth. The dentist places a rubber dam in the appropriate position in the patient's mouth and etches the enamel of the abutment teeth. The dentist then removes the prefabricated fiber-reinforced composite strip/filled composite pontic made from a "universal shade" composite (e.g., Vita shade A3 available from Vident, Brea, Calif.) from a darkened plastic bag and places it into the edentulous area. The dentist then adjusts the shape of the pontic as necessary while protecting the fiber-reinforced composite wings with their protective sleeves of darkened acetate. Unfilled resin is added to the proximal and lingual surfaces of the abutment teeth and a low-viscosity hybrid composite is placed between the pontic and the proximal tooth surfaces. The pontic is bonded to the proximal surfaces with light polymerization of approximately 90 seconds per side using a small 2 mm opening tip (such as a Demetron pin point light probe available from Ivoclar, Amherst, N.Y.).

More examples of hybrid components may be posts and pins which may include a cured section and an uncured section, such as the lower end which is to be bonded to the canal or other area in a patient's mouth.

The protective sleeves are removed from the fiber-reinforced composite wings one at a time, exposing the fiber-reinforced composite strips. Each strip is adapted carefully to the lingual or facial tooth surface while it is polymerized. The fiber-reinforced composite strips are, therefore, being adapted, bonded and polymerized at the same time. In addition to the uncured or slightly partially uncured wing or extensions, the perimeter of the cured section (pontic section or other section which is cured) may be left uncured or only slightly partially cured and covered with protective sleeves or other materials which will be uncovered at the time of use. The component or pontic will be placed within the area between the abutment teeth or other component to which it is to be attached and will readily bond to the abutment teeth or other component due to the fact that it had been left unpolymerized.

If necessary, the dentist then adds the correct shape of particulate composite to the pontic so that it is built to full contour and adds composite to the external surfaces of the fiber-reinforced composite strips, thereby covering the fiber-reinforced composite. The occlusion is adjusted and all of the composite is polished after the rubber dam is removed and the single-tooth replacement prosthesis is completed. Alternatively, as stated above, the pontic may be preformed to an appropriate anatomical shape having a cured center section whereby the periphery of the center section is uncured. The pontic is placed into position in the patient's mouth or in a plaster cast of the patient's mouth and forms the final proximal and apical shape.

As another example of a hybrid component, prefabricated bars such as bars 10, 12, 14 and 16 depicted in FIG. 1, may comprise sections of varying degrees of polymerization. The middle sections of the bars may be fully cured or partially cured to a degree of hardness for machining, cutting, carving or grinding. Sections at each end of the bars are uncured or only slightly partially cured and kept protected until ready for use. The uncured sections may be further modified at the point of use by forming, shaping, contouring, adjusting, and/or etching. The bars are useful in, for example, implant systems such as that shown in FIG. 13. Bars 132 may be hybrid bars with uncured end sections whereby the bars may be easily and readily bonded to cylinders 130 at the uncured sections. Likewise, cylinders 130 may include uncured sections, preferably at the shelf area whereat the cylinder and bar are in contact. The uncured sections are positioned in contact with respect to one another and thereafter cured, providing not only a strong, solid bond between the two components (130 and 132), but also a convenient and easy way to bond together the components.

As will be appreciated, the present invention provides preshaped, prefabricated cured components and hybrid components having optimum strength. The components may be ready-to-use structural components, structural components which may or may not be further modified prior to use, or components which must be further modified prior to use. The components are provided of varying shapes and sizes offering many options to the technician or practitioner in the fabrication of dental appliances. Due to the many different shapes, sizes and contours of teeth, a kit may be provided including ready-to-use structural components in the shape of pontics, rods and bars of varying configurations and sizes to offer the technician and practitioner options with which to construct dental appliances. Accordingly, custom made dental appliances can be easily fabricated using the ready-to-use structural components. The ready-to-use components may be further modified prior to fabrication of a dental appliance or restoration. Kits may also be provided with component blocks of varying shapes, sizes and colors offering many options to the technician and practitioner. The components may be used for the fabrication of orthodontic retainers, bridges, space maintainers, tooth replacement appliances, splints, crowns, partial crowns, dentures, posts, teeth, jackets, inlays, onlays, facings, veneers, facets, implants, cylinders, abutments, posts, pins, and connectors.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A ready-to-use component for use in the fabrication of a dental appliance system comprising:
a one-piece hybrid component having two or more sections of prefabricated preshaped fiber-reinforced composite material comprising a polymeric matrix and a reinforcing fiber component wherein at least one of the two or more sections is cured to a hardness for use in the dental appliance system and wherein at least one of the two or more sections is uncured.

2. The component of claim 1 wherein the at least one uncured section is slightly partially cured.

3. The component of claim 1 wherein the two or more sections of prefabricated preshaped fiber-reinforced composite material are structurally shaped for immediate use in dental appliance systems.

4. The component of claim 1 wherein the component is modified by machining, cutting, carving, grinding, abrading, etching, silanating, veneering, bending, shaping contouring, forming, adjusting or a combination thereof.

5. The component of claim 1 wherein the shape of the component is selected from the group consisting of a square, rectangle, triangle, rhomboid, ovoid, and cylinder.

6. The component of claim 1 wherein the component is shaped in the form from the group consisting of blocks, bars, rods and pontics.

7. The component of claim 6 wherein the rods comprise pins, posts or mixtures thereof.

8. The component of claim 6 wherein the blocks, bars, rods and pontics are either straight or curved.

9. The component of the claim 1 wherein the reinforcing fiber component is selected from the group consisting of fibers, fabric and mixtures thereof.

10. The component of claim 9 wherein the fabric is either woven or nonwoven.

11. The ready-to-use component of claim 9 wherein the fibers comprise glass, carbon, graphite, polyaramid, polyester, polyamide fibers or mixtures thereof.

12. The component of claim 1 wherein the at least one of the two or more sections which is cured to a hardness for use in the dental appliance system has undergone partial polymerization.

13. The component of claim 1 wherein the at least one of the two or more sections which is cured to a hardness for use in the dental appliance system has undergone full polymerization.

14. The component of claim 1 wherein the at least one of the two or more sections which is cured to a hardness for use in the dental appliance system comprises a perimeter which is uncured.

15. The component of claim 14 wherein the coating comprises a veneer.

16. The component of claim 1 wherein the fiber reinforced composite material further comprises at least one filler material.

17. The component of claim 16 wherein the one or more layers of composite material comprises a constituent selected from the group of woven fabric, nonwoven fabric and mixtures thereof preimpregnated with a polymeric material.

18. The ready-to-use component of claim 14 wherein the filler material comprises silica, silicate glass, quartz, barium silicate, strontium silicate, barium borosilicate, strontium borosilicate, borosilicate, lithium silicate, amorphous silica, ammoniated or deammoniated calcium phosphate, alumina, zirconia, tin oxide, titania or mixtures thereof.

19. The component of claim 1 wherein the dental appliance system is selected from the group consisting of orthodontic retainers, bridges, space maintainers, tooth replacement appliances, splints, crowns, partial crowns, dentures, posts, teeth, jackets, inlays, onlays, facings, veneers, facets, implants, cylinders, abutments, pins and connectors.

20. The component of claim 1 further including a coating thereon.

21. The component of claim 20 wherein the veneer is fabricated of composite material.

22. The component of claim 1 wherein the fiber-reinforced composite material further includes one or more layers of composite material.

23. The component of claim 1 further including a constituent selected from the group of woven fabric, nonwoven fabric and mixtures thereof.

24. The component of claim 23 wherein the fabric is preimpregnated with a polymeric material.

25. The component of claim 1 wherein at least one of the two or more sections further comprises one or more layers of filled composite material.

26. The component of claim 1 wherein the ready-to-use component is a single unit pontic.

27. The component of claim 26 wherein the pontic comprises a middle pontic section and interproximal extensions.

28. The component of claim 27 wherein the middle pontic section is cured and the interproximal extensions are uncured or slightly partially cured.

29. The component of claim 1 wherein the ready-to-use component is a multiple unit pontic.

30. The component of claim 29 wherein the pontic includes interproximal extensions between the multiple units and on ends of the pontic.

31. A dental restoration comprising the ready-to-use component of claim 1.

32. The dental restoration of claim 31 wherein the ready-to-use component is modified prior to incorporation into the dental restoration.

33. An implant system comprising one or more sections manufactured from one or ore ready-to-use components of claim 1.

34. The implant system of claim 33 wherein sections comprise abutment, cylinders, and frameworks.

35. The implant system of claim 33 wherein the sections further comprise hybrid bars comprising a cured middle section and uncured end sections.

36. The ready-to-use component of claim 1 wherein the polymeric matrix comprises a polyamide, polyester, polyolefin, polyimide, polyarylate, polyurethane, vinyl ester, epoxy-based material, styrene, stryrene acrylonitrile, acrylonitrile butadiene styrene (ABS), polysulfone, polyacetal, polycarbonate, polyphenylene sulfide, or a mixture thereof.

37. The ready-to-use component of claim 1 wherein the polymeric matrix comprises an acrylic monomer, a methacrylic monomer or a mixture thereof.

38. The ready-to-use component of claim 1 wherein the polymeric matrix comprises the condensation product of bisphenol A and glycidyl methacrylate, 2,2'-bis[4-(3-methacryloxy-2-hydroxy propoxy)-phenyl]-propane, polyurethane dimethacrylates, triethylene glycol dimethacrylate, polyethylene glycol dimethacrylate, polycarbonate dimethacrylate, ethoxylated bisphenol A dimethacrylate or a mixture thereof.

39. The ready-to-use component of claim 1 wherein the polymeric matrix comprises polymerization initiators, polymerization accelerators, ultraviolet light absorbers, antioxidants, or mixtures thereof.

40. A kit for the fabrication of a dental appliance comprising:
one or more ready-to-use components for use in the fabrication of a dental appliance system wherein the one or more ready-to-use components comprises a one-piece hybrid component having two or more sections of prefabricated preshaped fiber-reinforced composite material comprising a polymeric matrix and a reinforcing fiber component wherein at least one of the two or more sections is cured to a hardness for use in the dental appliance system and wherein at least one of the two or more sections is uncured.

41. The kit of claim 40 wherein the components are shaped in a variety of forms comprising pontics, rods and bars.

42. The kit of claim 41 further including components shaped in the form of blocks.

43. The kit of claim 42 wherein the blocks comprise a variety of different dimensions and different cross-sectional configurations.

44. The kit of claim 42 wherein the blocks comprise a variety of different shades.

45. The kit of claim 41 wherein the pontics are single unit and multiple unit pontics.

46. The kit of claim 41 wherein the bars, rods and pontics comprise a variety of different dimensions and different cross-sectional configurations.

47. The kit of claim 41 wherein the bars, rods and pontics are of a variety of different shades.

48. The kit of claim 41 further comprising composite material, fiber-reinforced composite material and filler material.

49. A method of making a ready-to-use component for a dental appliance comprising:
preparing a mold for the desired shape of the component; wherein the mold comprises at least a first and a second section;
placing a first amount of composite material into the first section;
curing or partially curing the composite material;
placing a second amount of composite material into the first and second sections;
curing the second amount of composite material in the first section, whereby the second amount of composite material in the second section remains uncured;
covering the uncured second section with a protective cover to prevent curing until use.

50. A method of making a dental restoration for direct application into a patient's mouth comprising:
providing a ready-to-use component comprising two or more sections of prefabricated preshaped fiber-reinforced composite material comprising a polymeric matrix and a reinforcing fiber component wherein at least one of the two or more sections is cured to a hardness for use in the dental appliance system, wherein at least one of the two or more sections is uncured; and wherein the at least one uncured section is covered with a protective cover;
applying a bonding agent to one or more of the patient's teeth proximate an area for insertion of the ready-to-use component;
removing the protective cover from the at least one uncured section;
inserting the ready-to-use component in the patient's mouth and bonding the at least one uncured sections to the one or more of the patient's teeth to provide a dental restoration.

51. The method of claim 50 further comprising applying composite material to one or more the sections of the ready-to-use component in the patient's mouth.

52. A method of making a dental restoration for indirect application into a patient's mouth comprising:
providing a ready-to-use component comprising two or more sections of prefabricated preshaped fiber-reinforced composite material comprising a polymeric matrix and a reinforcing fiber component wherein at least one of the two or more sections is cured to a hardness for use in the dental appliance system, wherein at least one of the two or more sections is uncured; and wherein the at least one uncured section is covered with a protective cover;
applying a bonding agent to one or more of the patient's teeth proximate an area for insertion of the ready-to-use component;
removing the protective cover from the at least one uncured section;
inserting the ready-to-use component in the patient's mouth and bonding the at least one uncured sections to the one or more of the patient's teeth to provide a dental restoration the patient's mouth.

53. A ready-to-use component in the fabrication of a dental appliance system comprising:
a one-piece hybrid component having at least one cured section and at least one uncured section;
wherein the cured section comprises a first layer of fiber-reinforced composite material, a second layer of fiber-reinforced composite material, and a third layer of filled composite material; and
wherein the second layer of fiber-reinforced composite material extends into the at least one uncured section.

54. The ready-to-use component of claim 53 wherein the uncured section is slightly partially cured.

55. The ready-to-use component of claim 53 wherein the cured section comprises a section of the perimeter thereof which is partially cured.

56. The ready-to-use component of claim 53 wherein the first layer of fiber-reinforced composite material comprises short, randomly dispersed fibers.

57. The ready-to-use component of claim 53 wherein the second layer of fiber-reinforced composite material comprises longitudinally extending fibers.

58. A ready-to-use component in the fabrication of a dental appliance system comprising:

a one-piece hybrid component having at least one cured section and at least one uncured section;

wherein the cured section comprises a first layer of filled composite material, a second layer of fiber-reinforced composite material, and a third layer of filled composite material; and wherein the second layer of fiber-reinforced composite material extends into the at least one uncured section.

59. A ready-to-use component in the fabrication of a dental appliance system comprising:

a one-piece hybrid component having at least one cured section and at least one uncured section;

wherein the cured section comprises a first layer of fiber-reinforced composite material, a second layer of fiber-reinforced composite material, and a third layer of fiber-reinforced composite material; and wherein the second layer of fiber-reinforced composite material extends into the at least one uncured section.

* * * * *